United States Patent [19]

Lin et al.

[11] 4,093,716

[45] June 6, 1978

[54] COMPOSITIONS CONTAINING 5-AMINO-5-DEOXYTHYMIDINE AND PHARMACEUTICALLY ACCEPTABLE SALTS THEREOF

[75] Inventors: Tai-Shun Lin, North Haven; H. William Prusoff, Branford; David C. Ward, Guilford, all of Conn.

[73] Assignee: Research Corporation, New York, N.Y.

[21] Appl. No.: 792,047

[22] Filed: Apr. 28, 1977

[51] Int. Cl.² .................. A61K 31/70; C07H 19/06
[52] U.S. Cl. .................................. 424/180; 536/23
[58] Field of Search .................. 424/180, 181; 536/23

[56] References Cited

PUBLICATIONS

Logue et al., "Jour. of the American Chem. Soc.", vol. 94, 4-19-72, pp. 2842-2843.
Cheng, "Chem. Abstracts", vol. 80, 1974, pp. 142, 302(a).

Primary Examiner—Johnnie R. Brown
Attorney, Agent, or Firm—Cooper, Dunham, Clark, Griffin & Moran

[57] ABSTRACT

The known compound 5'-amino-5'-deoxythymidine and the pharmaceutically acceptable acid addition salts thereof are potent inhibitors of herpes simplex virus and compositions containing one or more of them are therapeutically useful.

4 Claims, No Drawings

COMPOSITIONS CONTAINING 5-AMINO-5-DEOXYTHYMIDINE AND PHARMACEUTICALLY ACCEPTABLE SALTS THEREOF

The invention described herein was made in the course of work under a grant or award from the Department of Health, Education and Welfare.

BACKGROUND OF THE INVENTION

Herpes simplex viruses are the causative agents in a number of mammalian infections, for example, such human diseases as keratitis, herpes labialis (cold sores), cutaneous herpes, herpes zoster, herpes genitalis, herpes encephalitis, neonatal herpes, herpetic whitlow and acute herpetic gengivostomatitis. Poxviruses, especially poxvirus variolae, are the causative agents of smallpox in man. No completely satisfactory antiviral agent combining high potency and low toxicity has yet been discovered. Accordingly, considerable research effort has been expended in attempts to discover a suitable agent.

THE INVENTION

It has now been discovered that known compounds selected from the group consisting of 5'-amino-5'-deoxythymidine and its pharmaceutically acceptable acid addition salts are potent inhibitors of herpes simplex virus, and are substantially non-toxic. For convenience, this compound will hereinafter be referred to as $H_2NTdr$. This invention relates to these compounds and to therapeutically useful compositions containing one or more of them, whether or not associated with other therapeutically active ingredients.

The preparation of $H_2NTdr$ is described in an article by Horowitz et al in The Journal of The American Chemical Society, 27, 3065 (1962). Pharmaceutically acceptable acid addition salts are readily prepared by treatment of the basic compound with acid in aqueous media followed by evaporation of the solvent, for example, by freeze drying. The salts are generally more soluble than the free base, and are often preferred for the preparation of water based dosage forms such as eye drops. For example, a suspension of free amine in distilled water may be treated with an equivalent amount of aqueous acid, and the resulting solution stabilized with a buffer, such as phosphate buffered saline.

The acids which may be used to prepare the pharmaceutically acceptable acid addition salts of this invention are those containing non-toxic anions and include, for example, hydrochloric, sulfuric, phosphoric, acetic, lactic, citric, tartaric, oxalic, succinic, maleic, gluconic, saccharic and the like. The preparation of the salts is illustrated in the example.

Example 1

Acid Addition Salts

A total of 177 mg of 5'-amino-5'-deoxythymidine is suspended in distilled water and 0.55 ml of 1 M HCl added slowly with stirring to provide a solution of the amine hydrochloride salt. The salt is recovered by freeze-drying.

Other acid addition salts, specifically the salts of sulfuric, phosphoric, acetic, lactic, citric and tartaric are similarly prepared.

The products of this invention are administered with pharmaceutically acceptable, non-toxic carriers, the proportions of which are determined by the suitability and chemical nature of the particular carrier, the chosen route of administration, and standard pharmaceutical practice. For example, in combatting various infections or in maintaining therapeutically effective levels in blood or tissues, they may be administered orally in the form of tablets or capsules containing such excipients as starch, milk sugar, certain types of clay, etc. They may be enteric coated so as to be more resistant to the acid and digestive enzymes of the stomach. For intravenous and intramuscular administration they may be used in the form of a sterile solution containing other solutes, for example, enough saline or glucose to make the solution isotonic. A wide variety of dosage unit forms are possible.

The physician or veterinarian in attendance will determine the dosage regimen which will be effective. This will depend upon such factors as the age and weight of the patient, the degree and locus of the infection and the dosage unit form selected. Dosage unit forms containing from 25 to 250 mg are useful.

The compounds of this invention manifest a high order of inhibition with various herpes simplex viruses. For example, when tested against strain HSV-1 (prototype) at a concentration of 400 $\mu$M the average log reduction in titre was 2.3, and against HSV-2 (prototype) it was 2.8. No cytotoxicity is evident even at treatment levels as high as 400 $\mu$M. Comparable compounds which have been suggested as antiviral agents do not combine high activity with low toxicity. For example, idoxuridine, while it shows a high order of activity at relatively low levels, is almost totally cytotoxic at a concentration of 50 $\mu$M.

Standard procedures were used to maintain the virus and the Vero cells. This included growth and titration by plaque assay as well as the replications of the virus in the presence of the test compounds. Cells were maintained and infected in Dulbecco's medium with 10% fetal calf serum.

For testing, the cells were infected with virus at a ratio of approximately 10 plaque forming units per cell. The viral inoculum was drained after one hour adsorption at 37° C. An appropriate volume of medium containing the compound for testing was added. After 36-48 hours at 37° C, the infected cells were frozen until ready for titration.

Acute toxicity of $H_2NTdr$ in mice indicates no toxicity at 1 g/kg of body weight. This figure coupled with the high order of activity indicates a good therapeutic index.

The compounds of this invention when used in appropriate dosage forms are particularly useful for the treatment of herpes simplex keratitis in mammals.

At the present time, the generally accepted therapy for acute herpes simplex keratitis includes the use of 5-iodo-deoxy-uridine (IdUrd). Although the clinical value of this compound has been well established, there is a need for alternative antiviral therapy for ocular herpetic infections. IdUrd-resistant strains of herpes simplex virus Type 1 have been found. Additionally, the compound exhibits significant cellular toxicity. This is manifested in undesirable side effects such as the development of follicular and papillary conjunctivitis, and epithelial punctate keratopathy.

For these and other reasons including teratogenicity of IdUrd which has been demonstrated in newborn rats following systemic administration and in pregnant rabbits receiving the drug topically to the eye in doses similar to those used clinically in humans, efforts have been made to find replacement therapeutics.

One advantage of $H_2NTdr$ is that it is effective in treating herpes simplex keratitis in rabbits and other mammals at a very low level.

Another advantage of the compound and its pharmaceutically acceptable salts is high solubility in aqueous preparations. It is soluble in physiological saline to the extent of 200 mg/ml, whereas IdUrd is soluble only to the extent of 5 mg/ml. This unexpectedly high solubility makes it possible to prepare highly concentrated dosage forms.

The following examples illustrate the typical dosage forms:

EXAMPLE 2

An aqueous solution is prepared by taking up 10 mg/ml of $H_2NTdr$ in 100 ml of water containing 1.4 g of polyvinyl alcohol, 5 g of chlorobutanol, and sufficient sodium chloride to make the solution isotonic.

EXAMPLE 3

A solution is prepared by taking up 1 g of the hydrochloride salt of $H_2NTdr$ in 100 ml of water containing 0.9 mg of benzalkonium chloride, 1 g of the disodium salt of ethylenediaminetetraacetic acid and sufficient sodium chloride to make the solution isotonic.

EXAMPLE 4

A solution is prepared by taking up 0.5 g of $H_2NTdr$ acetate in 100 ml of water containing 2 mg of ethyl mercury thiosalycilate and sufficient sodium chloride to make the solution isotonic.

EXAMPLE 5

An ointment is prepared thoroughly dispersing 5 g of $H_2NTdr$ in 100 g of white petrolatum containing 0.8 mg of phenylmercuric acetate.

What is claimed is:

1. A pharmaceutical composition containing an effective amount of a compound for treating herpes simplex virus infection in mammals, said compound being selected from the group consisting of 5'-amino-5'-deoxythymidine and the pharmaceutically acceptable acid addition salts thereof together with a pharmaceutically acceptable carrier.

2. A composition of claim 1 containing 5'-amino-5'-deoxythymidine.

3. A method of treating a herpes simplex virus infection in a host mammal afflicted with such infection which comprises administering to the said host an amount of a compound which is effective for treating a herpes simplex virus infection, said compound being selected from the group consisting of 5'-amino-5'-deoxythymidine and the pharmaceutically acceptable acid salts thereof.

4. A method as in claim 3 wherein the compound is 5'-amino-5'-deoxythymidine.

* * * * *